United States Patent
Ablett et al.

(10) Patent No.: US 11,688,492 B1
(45) Date of Patent: Jun. 27, 2023

(54) METHOD AND SYSTEM FOR AUTOMATED POPULATION OUTREACH

(71) Applicant: LUCE COMMUNICATIONS LLC, Mira Loma, CA (US)

(72) Inventors: Daniel Robert Ablett, Upland, CA (US); Joel Nathanael Luce, Southlake, TX (US)

(73) Assignee: LUCE COMMUNICATIONS LLC, Mira Loma, CA (US)

( * ) Notice: Subject to any disclaimer, the term of this patent is extended or adjusted under 35 U.S.C. 154(b) by 126 days.

(21) Appl. No.: 17/079,989

(22) Filed: Oct. 26, 2020

Related U.S. Application Data

(63) Continuation-in-part of application No. 16/698,353, filed on Nov. 27, 2019, now Pat. No. 10,820,163.
(Continued)

(51) Int. Cl.
*G16H 10/40* (2018.01)
*G16H 10/60* (2018.01)
(Continued)

(52) U.S. Cl.
CPC ....... *G16H 10/40* (2018.01); *G01N 33/57419* (2013.01); *G16H 10/60* (2018.01); *H04W 4/14* (2013.01)

(58) Field of Classification Search
CPC ....... H04W 88/06; H04W 4/80; H04W 76/14; H04W 84/12; H04W 88/02; H04W 76/10;
(Continued)

(56) References Cited

U.S. PATENT DOCUMENTS

| 4,240,547 A | 12/1980 | Taylor |
| 4,720,017 A | 1/1988 | Pestes |

(Continued)

FOREIGN PATENT DOCUMENTS

| DE | 196 21 785 A1 | 12/1996 |
| JP | H9-292392 A | 11/1997 |

(Continued)

OTHER PUBLICATIONS

I. M. Ott et al; "Stability of SARS-CoV-2 RNA in Nonsupplemented Saliva"; Emerging Infectious Diseases, vol. 27, No. 4, pp. 1146-1150; Apr. 2021 (5 pages).
(Continued)

*Primary Examiner* — Kwasi Karikari
(74) *Attorney, Agent, or Firm* — Osha Bergman Watanabe & Burton LLP

(57) ABSTRACT

A system may include various user devices coupled to a cellular network. Each user device may be associated with a respective member of a predetermined population. The system may further include a contact management server coupled to the cellular network. The contact management server may determine a previous contact event of a user device among the user devices. The contact management server may further determine a selection of a first contact type for contacting the user device. The first contact type may be different from a second contact type of the previous contact event. The contact management server may further transmit a command that triggers the contact event of the user device based on the first contact type.

18 Claims, 7 Drawing Sheets

Related U.S. Application Data

(60) Provisional application No. 62/771,720, filed on Nov. 27, 2018.

(51) Int. Cl.
*G01N 33/574* (2006.01)
*H04W 4/14* (2009.01)

(58) Field of Classification Search
CPC ....... H04W 4/12; H04W 24/08; H04W 24/00; H04W 8/24; H04W 4/08; H04W 68/00; H04W 12/50
See application file for complete search history.

(56) References Cited

U.S. PATENT DOCUMENTS

| | | | |
|---|---|---|---|
| 4,949,840 | A | 8/1990 | Brown |
| 5,150,971 | A | 9/1992 | Strong et al. |
| 5,607,101 | A | 3/1997 | Saito |
| 5,611,433 | A | 3/1997 | Levy |
| 5,620,097 | A | 4/1997 | Timmons, II et al. |
| 5,921,396 | A | 7/1999 | Brown, Jr. |
| 5,996,799 | A | 12/1999 | Garreth et al. |
| 6,447,463 | B1 | 9/2002 | Borkowski |
| 6,467,642 | B2 | 10/2002 | Mullens et al. |
| 6,491,160 | B2 | 12/2002 | Butler et al. |
| 6,569,676 | B1 | 5/2003 | Tripp et al. |
| 6,921,370 | B2 | 7/2005 | Zhou et al. |
| 6,928,793 | B2 | 8/2005 | Rutledge |
| 6,953,207 | B2 | 10/2005 | Raming |
| 6,978,891 | B2 | 12/2005 | Rutledge |
| 7,128,352 | B1 | 10/2006 | Phippen |
| 7,243,796 | B2 | 7/2007 | Grablick |
| 7,264,776 | B2 | 9/2007 | Guo et al. |
| 9,352,863 | B1 | 5/2016 | Bishop et al. |
| 2003/0008467 | A1 | 1/2003 | Kai et al. |
| 2016/0267256 | A1 | 9/2016 | Peltier |
| 2017/0061091 | A1* | 3/2017 | McElhinney .......... G16H 10/60 |
| 2017/0213005 | A1* | 7/2017 | Cox ........................ G16H 40/67 |
| 2017/0236063 | A1 | 8/2017 | Dorris et al. |

FOREIGN PATENT DOCUMENTS

| | | | |
|---|---|---|---|
| JP | 2000-241055 | A | 9/2000 |
| JP | 2002-215789 | A | 8/2002 |
| JP | 2004-125408 | A | 4/2004 |
| WO | 95/15493 | A1 | 6/1995 |
| WO | 2007/068277 | A1 | 6/2007 |

OTHER PUBLICATIONS

C. Trobajo-Sanmartin et al; "Self-Collection of Saliva Specimens as a Suitable Alternative to Nasopharyngeal Swabs for the Diagnosis of SARS-CoV-2 by RT-qPCR"; Journal of Clinical Medicine, pp. 1-9; Jan. 15, 2021 (9 pages).

O. Erster et al; "Improved sensitivity, safety, and rapidity of COVID-19 tests by replacing viral storage solution with lysis buffer"; Plos One, pp. 1-8; Mar. 30, 2021 (8 pages).

Jiangsu Bioperfectus Technologies Co. Ltd.; "COVID-19 Coronavirus Real Time PCR Kit; For Emergency Use Only; Instructions For Use; For in vito Diagnostic (IVD) Use; RX Only"; Catalog # JC10223-1NW-50T, Catalog # JC10223-1NW-25T; May 6, 2021 (30 pages).

Patent Abstracts of Japan, Publication No. H92-92392 A dated Nov. 11, 1997 (1 pages).

Patent Abstracts of Germany, Publication No. 19621786 A1 dated May 12, 1996 (1 pages).

Patent Abstracts of Japan, Publication No. 2002-215789 A dated Aug. 2, 2002 (2 pages).

Patent Abstracts of Japan, Publication No. 2000-241055 A dated Sep. 8, 2000 (2 pages).

Patent Abstracts of Japan, Publication No. 2004-125408 A dated Apr. 22, 2004 (2 pages).

"Hair Drug Test Kit Follicle", Medimpex United Inc., http://www.meditests.com/hairdrugtest.html, Sep. 11, 2007 (2 pages).

"Medaus Saliva Test Kits", Medaus Pharmacy, htt lp://www.medaus.com/p/401.html, Sep. 11, 2007 (3 pages).

"Personal Saliva Hormone Profile Test Kits", Osteoporosis, Menopause, Hormone Health Products, http://www.osteoporosis-med.com/testkit.htm, Sep. 11, 2007 (3 pages).

Ochnio, JJ et al., Particpant-collected, Mail-delivered Oral Fluid Specimans can Replace Traditional Serosurveys: A Demonstration-of-feasibility Survey of Hepatitis A Virus-specific Antibodies in Adults., Canadian Journal of Public Health, http://www.ncbi.nlm.nih.gov/pubmed/17278676, Jan.-Feb. 2007 (1 page).

Winer, R., "Concordance of Self-Collected and Clinician-collected Swab Samples for Detecting Human Papillomavirus DNA in Women 18 to 32 years of age", Department of Epidemiology, University of Washington Seattle, Jun. 2007 (10 pages).

Levy, Sharon., A Review of Internet-Based Home Drug-Testing Products for Parents, American Academy of Pediatrics, Apr. 4, 2004 (9 pages).

"Home DNA Test Kits", http://www.homedna-test.com, DNA Testing Centre, Sep. 11, 2007 (5 pages).

* cited by examiner

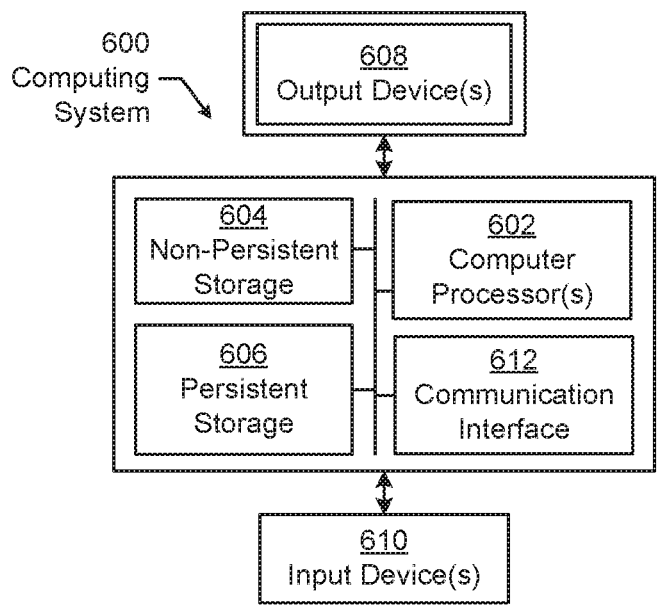
*FIG. 6.1*
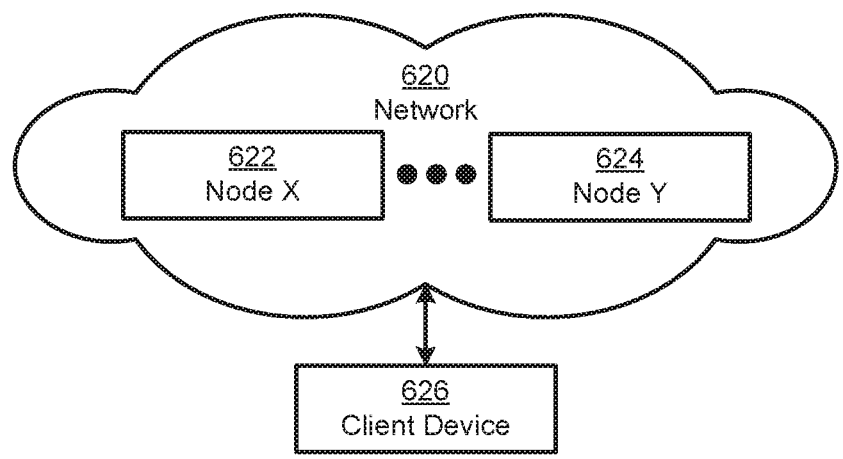
*FIG. 6.2*

METHOD AND SYSTEM FOR AUTOMATED POPULATION OUTREACH

CROSS-REFERENCE TO RELATED APPLICATIONS

This application claims priority to U.S. Provisional Patent Application Ser. No. 62/771,720, which was filed on Nov. 27, 2018. This application also claims the benefit of U.S. patent application Ser. No. 16/698,353, which was filed on Nov. 27, 2019, and issued as U.S. Pat. No. 10,820,163. Both applications are incorporated herein by reference.

BACKGROUND

Information can be relayed to users through multiple methods these days, such as through text messaging, automated voice recordings, and emails. However, different communication methods have different success rates in acquiring user responses as well as different costs for transmitting the information. For example, having a human operator manually make a live telephone call to a user has a much higher cost than an automated email reminder generated by a software application running on a server. However, the live telephone call may receive a higher response rate than the email reminder that may be distributed to the user's junk mail folder. Thus, technologies are sought that may manage and/or optimize various communication methods for performing outreach to different users.

SUMMARY

In general, in one aspect, embodiments relate to a method that includes obtaining, by a computer processor, a request to trigger a contact event of a user device. The user device is associated with a member of a predetermined population. The method includes determining, by the computer processor, a previous contact event of the user device. The method includes determining, by the computer processor, a selection of a first contact type for contacting the user device. The first contact type is different from a second contact type of the previous contact event. The method includes transmitting, by the computer processor, a command that triggers the contact event of the user device based on the selection of the first contact type.

In general, in one aspect, embodiments relate to a method that includes obtaining, by a contact management server, contact event result data regarding various user devices. The contact event result data describes results of various previous contact events regarding a predetermined member objective. The method includes determining, by the contact management server and based on the contact event result data, a subset of previous contact events that failed to result in members satisfying the predetermined member objective. The method includes determining, by the contact management server and based on the subset of previous contact events, a first contact type that is different from a second contact type associated with the subset of previous contact events. The method includes transmitting, by the contact management server, a command that trigger a contact event based on the first contact type.

In general, in one aspect, embodiments relate to a system that includes various user devices coupled to a cellular network. Each user device is associated with a respective member of a predetermined population. The system further includes a contact management server coupled to the cellular network. The contact management server determines a previous contact event of a user device among the user devices. The contact management server further determines a selection of a first contact type for contacting the user device. The first contact type is different from a second contact type of the previous contact event. The contact management server further transmits a command that triggers the contact event of the user device based on the first contact type.

Other aspects of the disclosure will be apparent from the following description and the appended claims.

BRIEF DESCRIPTION OF DRAWINGS

Specific embodiments of the disclosed technology will now be described in detail with reference to the accompanying figures. Like elements in the various figures are denoted by like reference numerals for consistency.

FIGS. 6.1 and 6.2 show a computing system in accordance with one or more embodiments.

DETAILED DESCRIPTION

Figure 1:
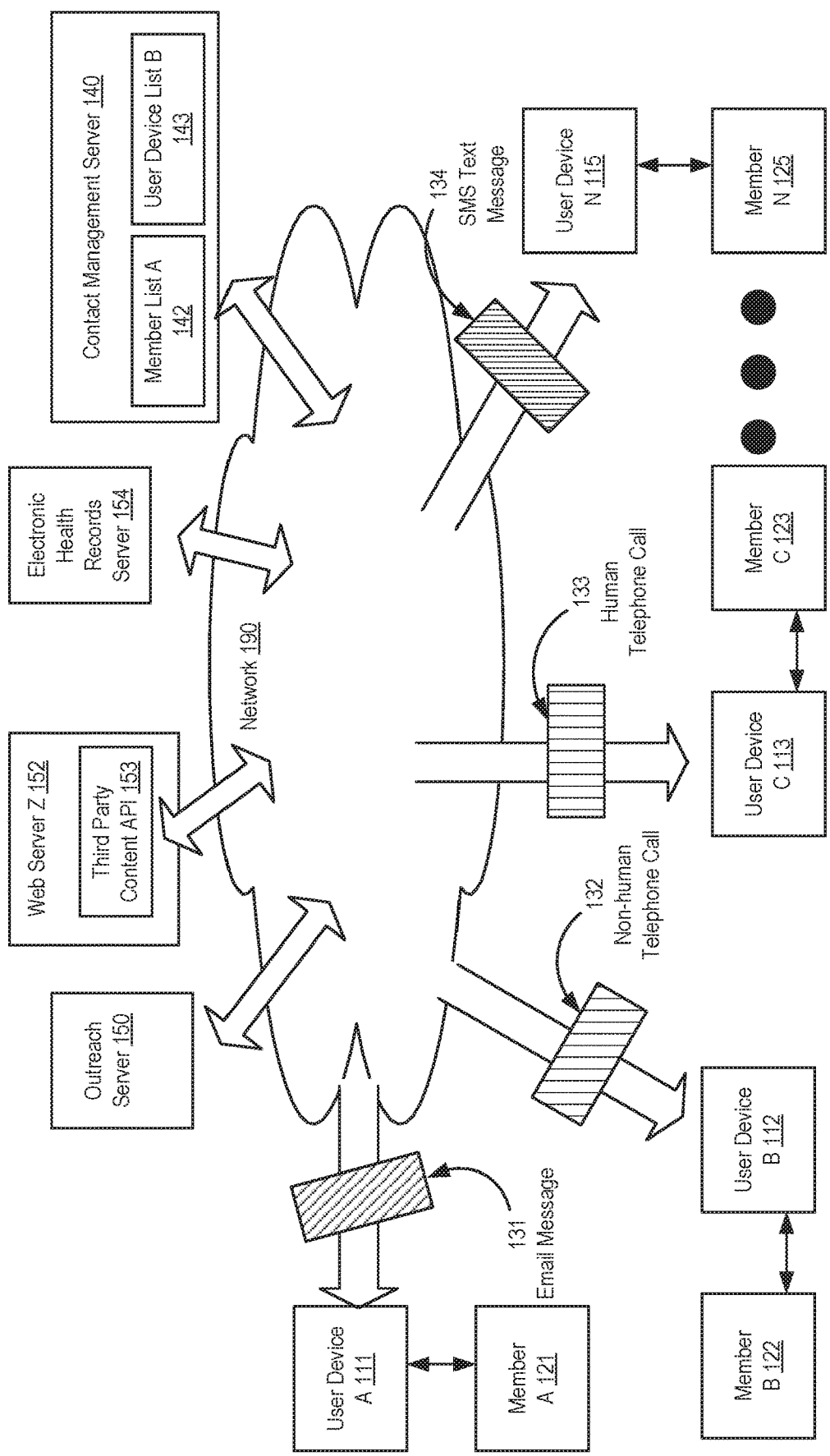
FIGS. 1 and 2 show block diagrams of systems in accordance with one or more embodiments.

Specific embodiments of the disclosure will now be described in detail with reference to the accompanying figures. Like elements in the various figures are denoted by like reference numerals for consistency.

In the following detailed description of embodiments of the disclosure, numerous specific details are set forth in order to provide a more thorough understanding of the disclosure. However, it will be apparent to one of ordinary skill in the art that the disclosure may be practiced without these specific details. In other instances, well-known features have not been described in detail to avoid unnecessarily complicating the description.

Throughout the application, ordinal numbers (e.g., first, second, third, etc.) may be used as an adjective for an element (i.e., any noun in the application). The use of ordinal numbers is not to imply or create any particular ordering of the elements nor to limit any element to being only a single element unless expressly disclosed, such as using the terms "before", "after", "single", and other such terminology. Rather, the use of ordinal numbers is to distinguish between the elements. By way of an example, a first element is distinct from a second element, and the first element may encompass more than one element and succeed (or precede) the second element in an ordering of elements.

In general, embodiments of the disclosure include systems and methods for managing communication with members of a population. For example, the system may include a cloud-computing environment in which a user can monitor and/or manage various communication activities and contact events attributed directly with population members. In one example, a remote server may schedule and automatically transmit commands that trigger various contact events among the population members. Contact events may include different contact types, such as SMS text messages, email messages, interactive voice response (IVR) telephone calls (also called "robocalls"), live person telephone calls, messages over a social networking platform, physical letters through postal service, etc.

In some embodiments, systems and methods manage contact events for a particular outreach program. Depending on the type of outreach program, for example, different contact types may be used to achieve one or more member objectives with members of the outreach program. As such, methods and systems are contemplated that connect members using various types of user devices, such as mobile devices and mobile applications. For example, a remote server may communicate with various members over smart phones, motor vehicles, desktop computers, etc.

In one embodiment, an outreach program may include a health plan organization that has multiple member objectives. More specifically, the health plan organization may be focused on communicating with patients of a health plan about one or more care gaps that individual patients need to address according to their health plan, e.g., medical screenings and/or clinical follow-ups. In particular, a member objective may correspond to return of a care gap kit to a laboratory or other testing facility. An example care gap kit may include an annual fecal immunochemical test (FIT) colorectal cancer screening designated for a predetermined date, e.g., a date generated with respect to an amount of time in relation to a patient's birthday. As such, some embodiments may track and identify whether a patient has performed one or more tests associated with the care gap kit.

Turning to FIG. 1, FIG. 1 shows a block diagram of a system in accordance with one or more embodiments. As shown in FIG. 1, a contact management server (e.g., contact management server (140)) may be a remote server that includes hardware and/or software with functionality for managing and triggering various contact events (e.g., email message (131), non-human telephone call (132), telephone call by a human operator (133), and a short message service (SMS) text message (134)) regarding various user devices various user devices (e.g., user device A (111), user device B (112), user device C (113), and user device N (115)). Contact events may include various types of messages for notifying users, such as reminders to perform some action, seeking to obtain a desired response from a respective user. In a medical patient context, a contact event may be referred to as patient-facing "touch." In one or more embodiments, for example, a contact event is successful where the member associated a contacted user device performs one or more tasks (e.g., providing a medical sample for a care gap kit) achieving the desired response to the contact event.

Furthermore, various members (e.g., member A (121), member B (122), member C (123), member D (125)) of a population are associated with various respective user devices (e.g., user device A (111), user device B (112), user device C (113), and user device N (115)). For example, a member may be a user who is part of a population where a contact management server controls and administers various communications with the population. Examples of populations may include members of a health plan within a geographical area, a targeted group for an advertising campaign, potential customers for a new product, eligible voters in a political district, etc. In some embodiments, members in a population are adjusted overtime, e.g., new members are added and previous members may be removed.

Keeping with FIG. 1, a contact management server may store contact information relating to various user devices (e.g., user device list B (143)) and/or members (e.g., member list A (142)) to identify recipients and other details of contact events. This contact information may include email addresses, phone numbers, website profiles (e.g., on a social networking site), user device accounts, scheduled dates for contact events, which populations a respective member is part of, contact event history, and other information relating to various contact of the respective member.

User devices (e.g., user device (290)) may include hardware and/or software for receiving inputs from a user and/or providing outputs to a user. Moreover, a user device may be coupled to one or more networks (e.g., network 190), where a contact event may be performed using a user device through such a network. For example, the network may include a cellular network, a local area network or wide area network (WAN) with access to the Internet, an online platform providing a social networking service, etc. Examples of user devices may include user equipment, personal computers, smartphones, motor vehicles, smart televisions, etc.

In some embodiments, a contact management server is coupled to one or more outreach servers (e.g., outreach server (150)). An outreach server may include hardware and/or software that collects and/or analyzes data regarding population members and their user devices. For example, an outreach server may be coupled to a laboratory facility for administering a clinical outreach program. After the laboratory provides a medical test, the outreach server may receive a notification that a member completed the medical test. Some examples of clinical outreach programs may include flu reminders, overdue doctor visits, diabetes control, etc. While clinical outreach programs are described, other embodiments are also contemplated for outreach programs outside the healthcare and medical field. In some embodiments, a content management server may operate one or more software applications that centralize the administration of various processes in an outreach program administered by one or more outreach servers.

In another embodiment, a contact management server may convey content securely between one or more secure databases e.g., databases for electronic health records located on an outreach server, and a centralized profile stored on the contact management server. Using a centralize profile, for example, a user may have dashboard visibility for member activity for a population associated with their profile.

In one or more embodiments, a contact management server is coupled to one or more application programming interfaces. For example, an application programming interface (API) may include one or more software programs that provide access to computing resources and data on servers and other computing devices. In one embodiment, the contact management server may be coupled to a third party content API (e.g., third party content API (153) disposed on web server Z (152)) that provides programmatic access to third party content, such as topical patient health education digital and video content.

As such, the third party content may be distributed to a contact management server using a cloud storage bucket. For example, a cloud storage bucket may define various types of content such as "article" content, "video" content, or "plain text" content as well segment definitions and bucket specific parameters. By using an API connection to third party content, the contact management server may integrate third party content into various outreach patient communications, such as contact events, that the contact management server manages for various populations. In one embodiment, the contact management server may have a pass-through mechanism where the third party content is transmitted to the contact management server then relayed using a contact event, such as a non-human telephone call or an email notification. In some embodiments, different types of third party content may be associated with a particular population and automatically incorporated by the contact management server into contact events.

In some embodiments, the contact management server may be use an API to couple with an electronic health record (EHR) system (e.g., electronic health records server (154)). For example, a request may be received from a user's EHR system to trigger automatically various communications, such as contact events. Likewise, upon receiving any records, such as electronic documents, of these communications, the contact management server may transmit the records to an EHR system. Thus, records obtained regarding members of a population may also be visible to users of the EHR system. The records may correspond to contact event result data and/or be a processed output using contact event result data.

Moreover, a contact management server may use multifactor authentication to insure only authorized users view member information and/or population information. Accordingly, a contact management server, an outreach server, a web server, an electronic health records server, and user devices may be similar to a computing system (600) described below in FIGS. 6.1 and 6.2 and the accompanying description.

Figure 2:
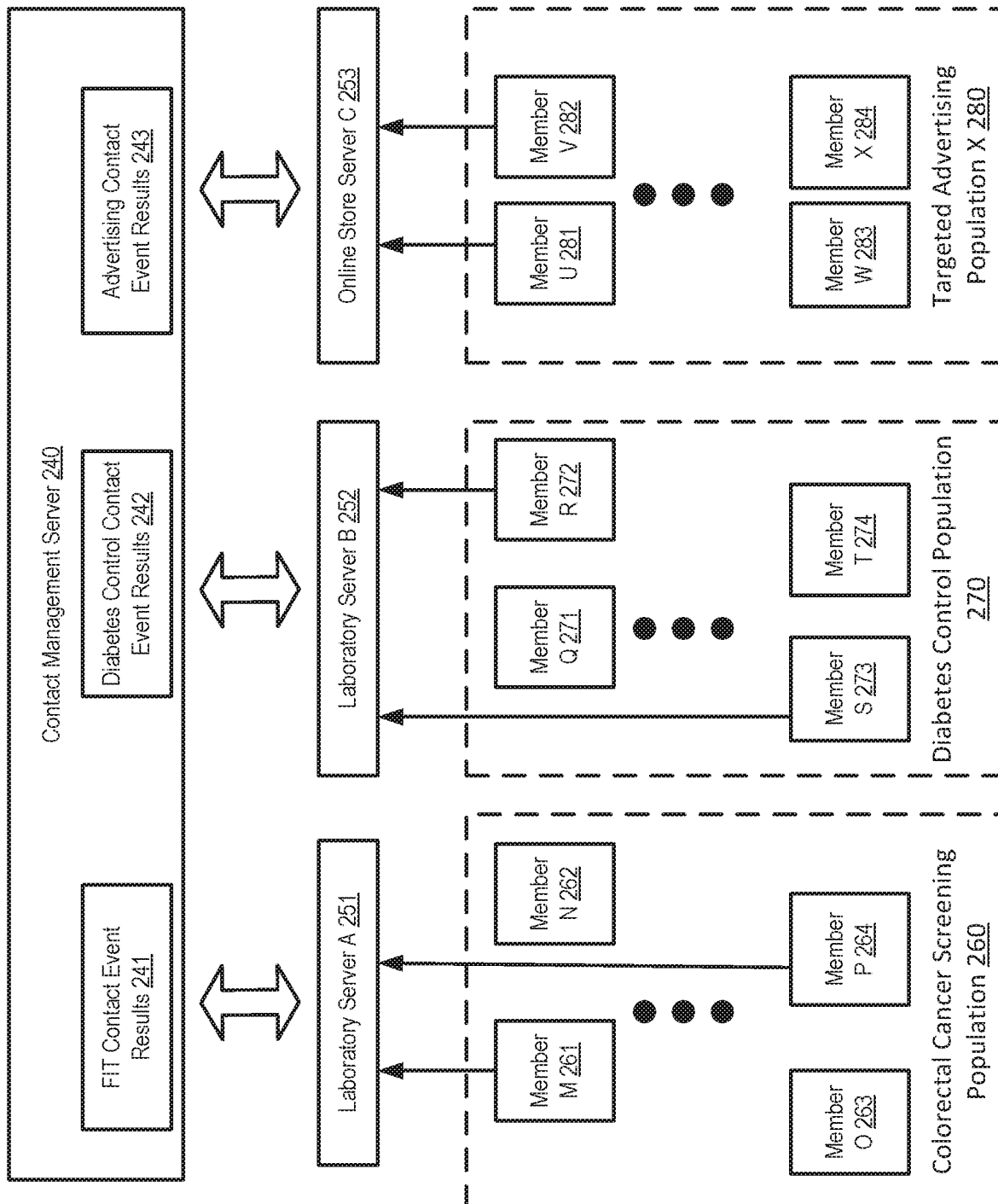

Turning to FIG. 2, FIG. 2 shows a block diagram of a system in accordance with one or more embodiments. As shown in FIG. 2, a contact management server may communicate with various outreach servers (e.g., laboratory server A (251), laboratory server B (252), and online store server C (253)) to manage contact operations for various populations (e.g., colorectal cancer (CRC) screening population (260), diabetes control population (270), targeted advertising population (280)). As such, the colorectal cancer screen population (260) may include member M (261), member N (262), member O (263), and member P (264). On the other hand, the diabetes control population (270) may include member Q (271), member R (272), member S (273), and member T (274). Likewise, a targeted advertising population (280) may include member U (281), member V (282), member W (283), and member X (284). Accordingly, the contact management server (240) may include functionality for reporting results and/or automating follow-up contact events to non-responders of multiple populations according to different and/or overlapping member objectives.

As shown in FIG. 2, the contact management server (240) may schedule contact events for these populations (260, 270, 280) with different member objectives. For example, the CRC screening population (260) may have as a member objective for members to perform an fecal immunochemical test (FIT) using a FIT kit, and return the FIT kit to a laboratory for testing. Thus, the laboratory may be coupled to laboratory server A (251). In some embodiments, the contact management server (240) provides a centralized connection point for lab data to be transmitted with laboratory results. The diabetes control population (270) may have a similar member objective, where members of the diabetes control population may be required to visit a medical facility to provide a blood sample for a diabetes blood glucose test. Thus, the contact management server (240) may assist in performing diabetes management with members of the diabetes control population (270). As shown in FIG. 2, member N (261) and member P (264) of the CRC screening population (260) have satisfied their population's member objective, while member R (272) and member S (273) have satisfied their population's member objective. However, the remaining members in the populations (260, 270) have not yet satisfied their respective member objectives. Accordingly, the contact management server (240) may store information (e.g., FIT contact event results (241), diabetes control contact event results (242)) regarding which members have and have not satisfied their member objectives.

In some embodiments, members may be located in two or more populations. For example, a blood glucose test may also be performed using the same or different self-test kit as an annual FIT screening. Thus, multiple member objectives may be satisfied with the same activity. Likewise, a contact management server may also manage various sub-populations with respective member sub-objectives. For example, while a population may correspond to members with diabetes, members within the population may be further categorized based on type of diabetes, age group, gender, geographical location, etc. Different sub-populations may also have their own corresponding sub-objectives that can be tracked and managed by the contact management server.

In a medical context, a contact management server may include functionality for the following: (1) sending a member a self-test kit; (2) obtaining a sample with the self-test kit for analysis at a laboratory; (3) recording receipt of the sample and triggering processing of the results of the sample analysis; and (4) recording the success of the contact event within a respective outreach program to satisfy downstream systems measuring quality of care for the respective patient and/or a population within the respective outreach program.

In another embodiment, the contact management server (240) manages contact events of targeted advertising population X (280) for an online store server C (253). The targeted advertising population X (280) includes member U (281), member V (282), member W (283), and member X (284). Here, the member objective for the targeted advertising population (280) may include purchasing a particular product from a company that controls online store server C (253). For example, when member U (281) and member V (282) make purchases through the online store server C (253), the contact management server (240) may receive a notification of the purchases from the online store server C (253). As such, the contact management server (240) may update advertising contact event results (243) accordingly based on the purchases.

In one or more embodiments, the contact management server (240) includes functionality for administering various processes for systematically defining and automating a series of contact events with a particular member. In response to detecting that a member has not performed a requested activity under a member objective, e.g., no sample from a self-testing kit has been received or analyzed by a laboratory, the contact management server (240) may automatically schedule another contact event that is the same contact type or of a different contact type for the member.

While FIGS. 1 and 2 show various configurations of components, other configurations may be used without departing from the scope of the disclosure. For example, various components in FIGS. 1 and 2 may be combined to create a single component. As another example, the functionality performed by a single component may be performed by two or more components.

Figure 3:
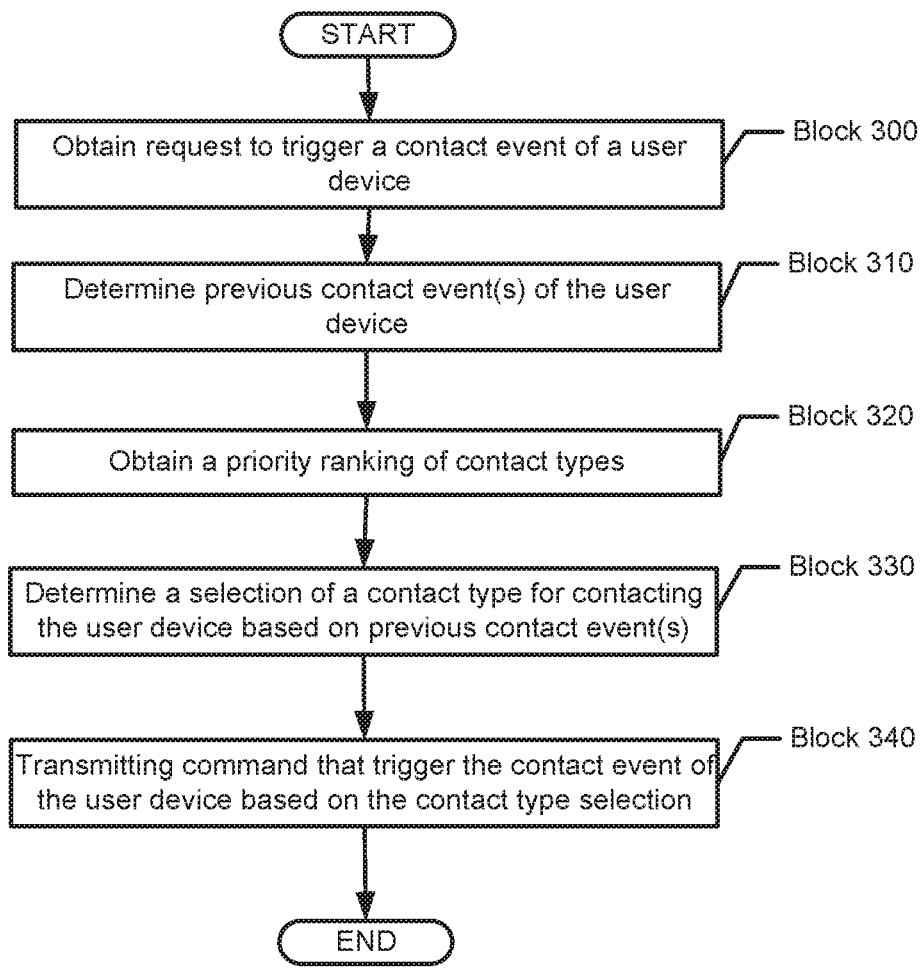
FIGS. 3 and 4 show flowcharts in accordance with one or more embodiments.

Turning to FIG. 3, FIG. 3 shows a flowchart in accordance with one or more embodiments. Specifically, FIG. 3 describes a general method for managing contact events for a user device. One or more blocks in FIG. 3 may be performed by one or more components (e.g., contact management server (140)) as described in FIGS. 1 and 2. While the various blocks in FIG. 3 are presented and described sequentially, one of ordinary skill in the art will appreciate that some or all of the blocks may be executed in different orders, may be combined or omitted, and some or all of the blocks may be executed in parallel. Furthermore, the blocks may be performed actively or passively.

In Block 300, a request to trigger a contact event of a user device is obtained in accordance with one or more embodiments. For example, a user may access over the Internet a centralized profile on a remote server with various contact event settings. The centralized profile may manage contact events for various members in a particular population that the user is granted privileges for managing. As such, the user may individually send requests to the contact management server to adjust contact event settings regarding scheduled dates/times and parameters for automatically transmitting commands to trigger contact events.

In some embodiments, the contact management server performs an algorithm, such as a machine learning algorithm, to determine which contact types have the highest degree of success for a particular member or population. Likewise, the remote server may automatically send a request to perform a contact event based on comparing one or more population profiles with an incumbent profile. Based on the degrees of contact event effectiveness for different contact event settings, a remote sever can automate the process.

In Block 310, one or more previous contact events of a user device are determined in accordance with one or more embodiments. For example, user devices may be contacted using multi-modal communication capabilities for multiple contact types: print/mail, email, SMS text, non-human telephone calls based on interactive voice responses ("robocalls"), telephone calls with human operators, communication services provides by mobile devices and/or mobile applications, etc. A server may analyze previous types of contact events, such as to identify whether a previous contact event should be repeated or a different contact event should be attempted for the user device. Previous contact events may be stored in a database that records contact event history for user devices and/or members.

In Block 320, a priority ranking of various contact types is obtained in accordance with one or more embodiments. In one embodiment, different contact types have static rankings that determine the order that certain types are triggered for contacting a user device. In some embodiments, the priority ranking is based on one or more characteristics of a population. Likewise, contact types in a priority ranking may be manually selected by a user with a centralized profile or automatically determined using one or more algorithms and contact event results from the respective population or similar populations. In some embodiments, the priority ranking is adjusted based on contact event result data.

In Block 330, a selection of a contact type for contacting a user device is determined based on one or more previous contact events in accordance with one or more embodiments. For example, based on a particular outreach program, a server may initiate contact of a member with a default contact event, such as a phone text message or a non-human telephone call. Depending on whether a response is detected for any previous contact events, the same contact event or a different contact event may be selected. For example, where a priority ranking is used to manage contact events, a server may automatically select a particular contact type for a specific number of times. After performing the contact type a specific number of times, a server may change to a different contact type according to the priority ranking. Thus, an iterative process may be performed to select and/or exclude particular contact types for use in managing a population.

In Block 340, a command is transmitted that triggers a contact event of a user device based on a selection of a contact type in accordance with one or more embodiments. For example, a server may have one or more applications that have computer telephony integration, e.g., to generate an interactive voice response in a non-human telephone call. Here, a computer device may interact with members through the use of voice and dual-tone multi-frequency signaling (DTMF) tones input via a keypad. In some embodiments, telephony application programming interface (TAPI) may provide such computer telephony integration and enable a computer device to use telephone services. Thus, a server may perform a contact event or transmit a message to a different computer device to perform the contact event. Likewise, the contact event may result in an interaction between a server and a member via a telephone keypad or by speech recognition.

Figure 4:
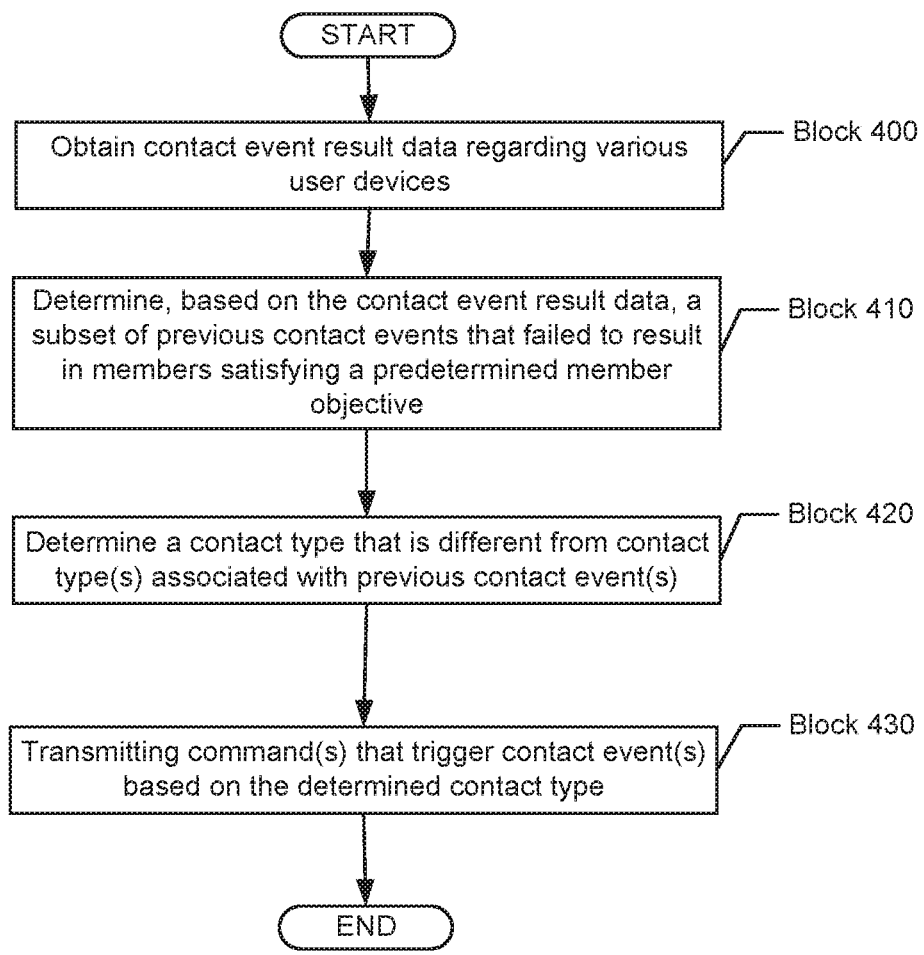

Turning to FIG. 4, FIG. 4 shows a flowchart in accordance with one or more embodiments. Specifically, FIG. 4 describes a general method for managing contact events for multiple user devices associated with a particular population. One or more blocks in FIG. 4 may be performed by one or more components (e.g., contact management server (140)) as described in FIGS. 1 and 2. While the various blocks in FIG. 4 are presented and described sequentially, one of ordinary skill in the art will appreciate that some or all of the blocks may be executed in different orders, may be combined or omitted, and some or all of the blocks may be executed in parallel. Furthermore, the blocks may be performed actively or passively.

In Block 400, contact event result data is obtained regarding various user devices in accordance with one or more embodiments. In some embodiments, a server may provide a standard point of intake for incoming data from one or more outreach servers. Thus, contact event result data may be aggregated, e.g., at a contact management server for performing an analysis and/or comparisons. In particular, contact event result data may include information that indicates whether a member objective was achieved in response to one or more contact events. Likewise, the contact event result data may indicate whether no success has occurred by a member following the contact event.

In Block 410, a subset of previous contact events are determined based on contact event result data that failed to result in members satisfying a predetermined member objective in accordance with one or more embodiments. For example, a server may analyze contact event result data to determine one or more subsets of contact events that satisfied or fails to achieve a member objective. A member subset that satisfied the predetermined member objective may be removed from the contact sequence, while members subsets that failed to satisfy the predetermined member objective may receive future contact events seeking a response accordingly.

In one embodiment, the member objective may be binary, e.g., a patient delivered a medical test sample to a laboratory or failed to deliver the sample. In other embodiments, the member objective may be scored using various attributes, e.g., how fast after a contact event was performed did the patient deliver the sample or how many times did the patient visitor a doctor within a predetermined time period. In some embodiments, the member objective is determined dynamically according to an algorithm, e.g., based on a machine learning model that optimizes contact sequences for a particular member or multiple members of a population.

In Block 420, a contact type is determined that is different from one or more contact types associated with one or more previous contact events in accordance with one or more embodiments. For example, if a previous contact event fails to cause a member to produce a desired response, a different contact type may be used in hope of achieving a different result. In some embodiments, a server may analyze contact event result data for one or more populations in order to optimize contact event performance. Thus, different contact types may be applied to a population's members in order to increase the contact event success rate.

In Block 430, one or more commands are transmitted that trigger one or more contact events based on a determined contact type in accordance with one or more embodiments. Block 430 may be performed in a similar manner as described above in Block 340 and the accompanying description.

Figure 5:
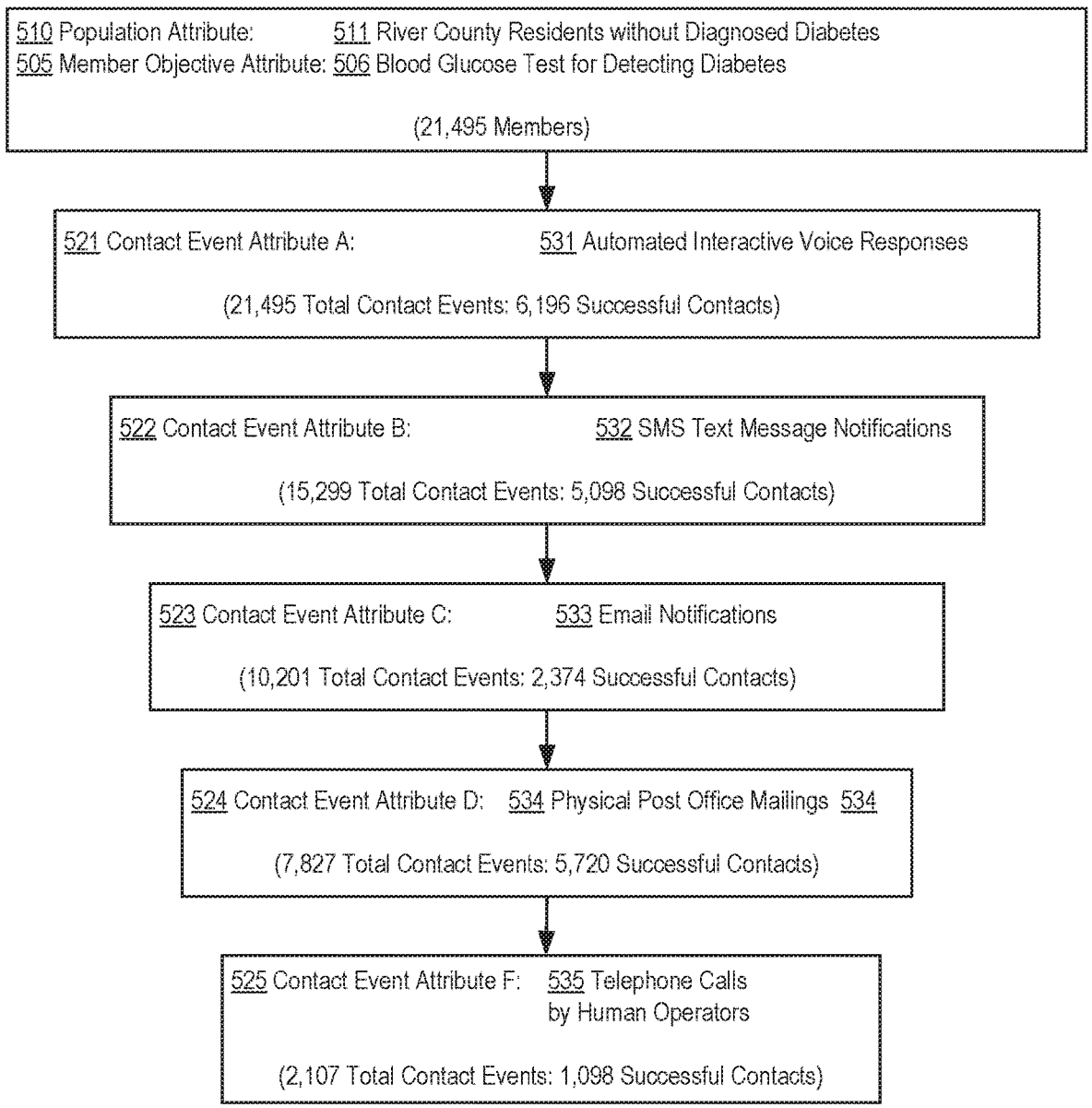
FIG. 5 shows an example in accordance with one or more embodiments.

Turning to FIG. 5, FIG. 5 provides an example of a contact sequence. The following example is for explanatory purposes only and not intended to limit the scope of the disclosed technology. Turning to FIG. 5, FIG. 5 shows a contact sequence R (500) that has a population attribute (510) corresponding to River County residents without diagnosed diabetes (511). The contact sequence R (500) has a member objective attribute (505) corresponding to members performing a specific blood glucose test (506) for detecting diabetes. As shown in FIG. 5, the population regarding the contact sequence R (500) has 21,495 total members.

Further, the contact sequence R (500) follows a priority ranking of contact types that is organized according to various contact event types (i.e., contact event type attribute A (521), contact event type attribute B (522), contact event type attribute C (523), contact event type attribute D (524), and contact event type attribute F (525)). In particular, contact events within the contact sequence R (500) follow a priority ranking where automated interactive voice responses (531) are performed first, then SMS text message notifications (532), then email notifications (533), then physical post office mailings (534), and finally telephone calls (535) by human operators.

Keeping with FIG. 5, for the automated interactive voice responses (531), 21,495 total contact events were performed, which results in 6,196 successful contacts that satisfied the member objective attribute (505). The contact sequence R (500) then proceeds to use a different type of contact event, i.e., SMS text message notifications (532), rather than repeat the automated interactive voice recordings (531). With the SMS text message notifications (532), 15,299 contact events were performed, but only 2,374 successful contacts occurred among the total contact events. The contact sequence R (500) then proceeded to the email notifications (533), which included 10,201 total contact events and only 2,374 successful contacts. Next, the contact sequence R (500) proceeded with physical post office mailings (534) that included 7,827 total contact events resulting in 5,720 successful contacts. Finally, the contact sequence R (500) performed telephone calls (535) with human operators that included 2,107 total contact events and 1,098 successful contacts.

Computing System

Embodiments may be implemented on a computing system. Any combination of mobile, desktop, server, router, switch, embedded device, or other types of hardware may be used. For example, as shown in FIG. 6.1, the computing system (600) may include one or more computer processors (602), non-persistent storage (604) (e.g., volatile memory, such as random access memory (RAM), cache memory), persistent storage (606) (e.g., a hard disk, an optical drive such as a compact disk (CD) drive or digital versatile disk (DVD) drive, a flash memory, etc.), a communication interface (612) (e.g., Bluetooth interface, infrared interface, network interface, optical interface, etc.), and numerous other elements and functionalities.

The computer processor(s) (602) may be an integrated circuit for processing instructions. For example, the computer processor(s) may be one or more cores or micro-cores of a processor. The computing system (600) may also include one or more input devices (610), such as a touchscreen, keyboard, mouse, microphone, touchpad, electronic pen, or any other type of input device.

The communication interface (612) may include an integrated circuit for connecting the computing system (600) to a network (not shown) (e.g., a local area network (LAN), a wide area network (WAN) such as the Internet, mobile network, or any other type of network) and/or to another device, such as another computing device.

Further, the computing system (600) may include one or more output devices (608), such as a screen (e.g., a liquid crystal display (LCD), a plasma display, touchscreen, cathode ray tube (CRT) monitor, projector, or other display device), a printer, external storage, or any other output device. One or more of the output devices may be the same or different from the input device(s). The input and output device(s) may be locally or remotely connected to the computer processor(s) (602), non-persistent storage (604), and persistent storage (606). Many different types of computing systems exist, and the aforementioned input and output device(s) may take other forms.

Software instructions in the form of computer readable program code to perform embodiments of the disclosure may be stored, in whole or in part, temporarily or permanently, on a non-transitory computer readable medium such as a CD, DVD, storage device, a diskette, a tape, flash memory, physical memory, or any other computer readable storage medium. Specifically, the software instructions may correspond to computer readable program code that, when executed by a processor(s), is configured to perform one or more embodiments of the disclosure.

The computing system (600) in FIG. 6.1 may be connected to or be a part of a network. For example, as shown in FIG. 6.2, the network (620) may include multiple nodes (e.g., node X (622), node Y (624)). Each node may correspond to a computing system, such as the computing system shown in FIG. 6.1, or a group of nodes combined may correspond to the computing system shown in FIG. 6.1. By way of an example, embodiments of the disclosure may be implemented on a node of a distributed system that is connected to other nodes. By way of another example, embodiments of the disclosure may be implemented on a distributed computing system having multiple nodes, where each portion of the disclosure may be located on a different node within the distributed computing system. Further, one or more elements of the aforementioned computing system (600) may be located at a remote location and connected to the other elements over a network.

Although not shown in FIG. 6.2, the node may correspond to a blade in a server chassis that is connected to other nodes via a backplane. By way of another example, the node may correspond to a server in a data center. By way of another example, the node may correspond to a computer processor or micro-core of a computer processor with shared memory and/or resources.

The nodes (e.g., node X (622), node Y (624)) in the network (620) may be configured to provide services for a client device (626). For example, the nodes may be part of a cloud computing system. The nodes may include functionality to receive requests from the client device (626) and transmit responses to the client device (626). The client device (626) may be a computing system, such as the computing system shown in FIG. 6.1. Further, the client device (626) may include and/or perform all or a portion of one or more embodiments of the disclosure.

The computing system or group of computing systems described in FIGS. 6.1 and 6.2 may include functionality to perform a variety of operations disclosed herein. For example, the computing system(s) may perform communication between processes on the same or different systems. A variety of mechanisms, employing some form of active or passive communication, may facilitate the exchange of data between processes on the same device. Examples representative of these inter-process communications include, but are not limited to, the implementation of a file, a signal, a socket, a message queue, a pipeline, a semaphore, shared memory, message passing, and a memory-mapped file. Further details pertaining to a couple of these non-limiting examples are provided below.

Based on the client-server networking model, sockets may serve as interfaces or communication channel endpoints enabling bidirectional data transfer between processes on the same device. Foremost, following the client-server networking model, a server process (e.g., a process that provides data) may create a first socket object. Next, the server process binds the first socket object, thereby associating the first socket object with a unique name and/or address. After creating and binding the first socket object, the server process then waits and listens for incoming connection requests from one or more client processes (e.g., processes that seek data). At this point, when a client process wishes to obtain data from a server process, the client process starts by creating a second socket object. The client process then proceeds to generate a connection request that includes at least the second socket object and the unique name and/or address associated with the first socket object. The client process then transmits the connection request to the server process. Depending on availability, the server process may accept the connection request, establishing a communication channel with the client process, or the server process, busy in handling other operations, may queue the connection request in a buffer until the server process is ready. An established connection informs the client process that communications may commence. In response, the client process may generate a data request specifying the data that the client process wishes to obtain. The data request is subsequently transmitted to the server process. Upon receiving the data request, the server process analyzes the request and gathers the requested data. Finally, the server process then generates a reply including at least the requested data and transmits the reply to the client process. The data may be transferred, more commonly, as datagrams or a stream of characters (e.g., bytes).

Shared memory refers to the allocation of virtual memory space in order to substantiate a mechanism for which data may be communicated and/or accessed by multiple processes. In implementing shared memory, an initializing process first creates a shareable segment in persistent or non-persistent storage. Post creation, the initializing process then mounts the shareable segment, subsequently mapping the shareable segment into the address space associated with the initializing process. Following the mounting, the initializing process proceeds to identify and grant access permission to one or more authorized processes that may also write and read data to and from the shareable segment. Changes made to the data in the shareable segment by one process may immediately affect other processes, which are also linked to the shareable segment. Further, when one of the authorized processes accesses the shareable segment, the shareable segment maps to the address space of that authorized process. Often, one authorized process may mount the shareable segment, other than the initializing process, at any given time.

Other techniques may be used to share data, such as the various data described in the present application, between processes without departing from the scope of the disclosure. The processes may be part of the same or different application and may execute on the same or different computing system.

Rather than or in addition to sharing data between processes, the computing system performing one or more embodiments of the disclosure may include functionality to receive data from a user. For example, in one or more embodiments, a user may submit data via a graphical user interface (GUI) on the user device. Data may be submitted via the graphical user interface by a user selecting one or more graphical user interface widgets or inserting text and other data into graphical user interface widgets using a touchpad, a keyboard, a mouse, or any other input device. In response to selecting a particular item, information regarding the particular item may be obtained from persistent or non-persistent storage by the computer processor. Upon selection of the item by the user, the contents of the obtained data regarding the particular item may be displayed on the user device in response to the user's selection.

By way of another example, a request to obtain data regarding the particular item may be sent to a server operatively connected to the user device through a network. For example, the user may select a uniform resource locator (URL) link within a web client of the user device, thereby initiating a Hypertext Transfer Protocol (HTTP) or other protocol request being sent to the network host associated with the URL. In response to the request, the server may extract the data regarding the particular selected item and send the data to the device that initiated the request. Once the user device has received the data regarding the particular item, the contents of the received data regarding the particular item may be displayed on the user device in response to the user's selection. Further to the above example, the data received from the server after selecting the URL link may provide a web page in Hyper Text Markup Language (HTML) that may be rendered by the web client and displayed on the user device.

Once data is obtained, such as by using techniques described above or from storage, the computing system, in performing one or more embodiments of the disclosure, may extract one or more data items from the obtained data. For example, the extraction may be performed as follows by the computing system (600) in FIG. 6.1. First, the organizing pattern (e.g., grammar, schema, layout) of the data is determined, which may be based on one or more of the following: position (e.g., bit or column position, Nth token in a data stream, etc.), attribute (where the attribute is associated with one or more values), or a hierarchical/tree structure (consisting of layers of nodes at different levels of detail—such as in nested packet headers or nested document sections). Then, the raw, unprocessed stream of data symbols is parsed, in the context of the organizing pattern, into a stream (or layered structure) of tokens (where each token may have an associated token "type").

Next, extraction criteria are used to extract one or more data items from the token stream or structure, where the extraction criteria are processed according to the organizing pattern to extract one or more tokens (or nodes from a layered structure). For position-based data, the token(s) at the position(s) identified by the extraction criteria are extracted. For attribute/value-based data, the token(s) and/or node(s) associated with the attribute(s) satisfying the extraction criteria are extracted. For hierarchical/layered data, the token(s) associated with the node(s) matching the extraction criteria are extracted. The extraction criteria may be as simple as an identifier string or may be a query presented to a structured data repository (where the data repository may be organized according to a database schema or data format, such as XML).

The extracted data may be used for further processing by the computing system. For example, the computing system of FIG. 6.1, while performing one or more embodiments of the disclosure, may perform data comparison. Data comparison may be used to compare two or more data values (e.g., A, B). For example, one or more embodiments may determine whether A>B, A=B, A !=B, A<B, etc. The comparison may be performed by submitting A, B, and an opcode specifying an operation related to the comparison into an arithmetic logic unit (ALU) (i.e., circuitry that performs arithmetic and/or bitwise logical operations on the two data values). The ALU outputs the numerical result of the operation and/or one or more status flags related to the numerical result. For example, the status flags may indicate whether the numerical result is a positive number, a negative number, zero, etc. By selecting the proper opcode and then reading the numerical results and/or status flags, the comparison may be executed. For example, in order to determine if A>B, B may be subtracted from A (i.e., A−B), and the status flags may be read to determine if the result is positive (i.e., if A>B, then A−B>0). In one or more embodiments, B may be considered a threshold, and A is deemed to satisfy the threshold if A=B or if A>B, as determined using the ALU. In one or more embodiments of the disclosure, A and B may be vectors, and comparing A with B includes comparing the first element of vector A with the first element of vector B, the second element of vector A with the second element of vector B, etc. In one or more embodiments, if A and B are strings, the binary values of the strings may be compared.

The computing system in FIG. 6.1 may implement and/or be connected to a data repository. For example, one type of data repository is a database. A database is a collection of information configured for ease of data retrieval, modification, re-organization, and deletion. Database Management System (DBMS) is a software application that provides an interface for users to define, create, query, update, or administer databases.

The user, or software application, may submit a statement or query into the DBMS. Then the DBMS interprets the statement. The statement may be a select statement to request information, update statement, create statement, delete statement, etc. Moreover, the statement may include parameters that specify data, or data container (database, table, record, column, view, etc.), identifier(s), conditions (comparison operators), functions (e.g. join, full join, count, average, etc.), sort (e.g. ascending, descending), or others. The DBMS may execute the statement. For example, the DBMS may access a memory buffer, a reference or index a file for read, write, deletion, or any combination thereof, for responding to the statement. The DBMS may load the data from persistent or non-persistent storage and perform computations to respond to the query. The DBMS may return the result(s) to the user or software application.

The computing system of FIG. 6.1 may include functionality to present raw and/or processed data, such as results of comparisons and other processing. For example, presenting data may be accomplished through various presenting methods. Specifically, data may be presented through a user interface provided by a computing device. The user interface may include a GUI that displays information on a display device, such as a computer monitor or a touchscreen on a handheld computer device. The GUI may include various GUI widgets that organize what data is shown as well as how data is presented to a user. Furthermore, the GUI may present data directly to the user, e.g., data presented as actual data values through text, or rendered by the computing device into a visual representation of the data, such as through visualizing a data model.

For example, a GUI may first obtain a notification from a software application requesting that a particular data object be presented within the GUI. Next, the GUI may determine a data object type associated with the particular data object, e.g., by obtaining data from a data attribute within the data object that identifies the data object type. Then, the GUI may determine any rules designated for displaying that data object type, e.g., rules specified by a software framework for a data object class or according to any local parameters defined by the GUI for presenting that data object type. Finally, the GUI may obtain data values from the particular data object and render a visual representation of the data values within a display device according to the designated rules for that data object type.

Data may also be presented through various audio methods. In particular, data may be rendered into an audio format and presented as sound through one or more speakers operably connected to a computing device.

Data may also be presented to a user through haptic methods. For example, haptic methods may include vibrations or other physical signals generated by the computing system. For example, data may be presented to a user using a vibration generated by a handheld computer device with a predefined duration and intensity of the vibration to communicate the data.

The above description of functions presents only a few examples of functions performed by the computing system of FIG. 6.1 and the nodes and/or client device in FIG. 6.2. Other functions may be performed using one or more embodiments of the disclosure.

Automated Data Integration for Various Contact Types

Figure 7:
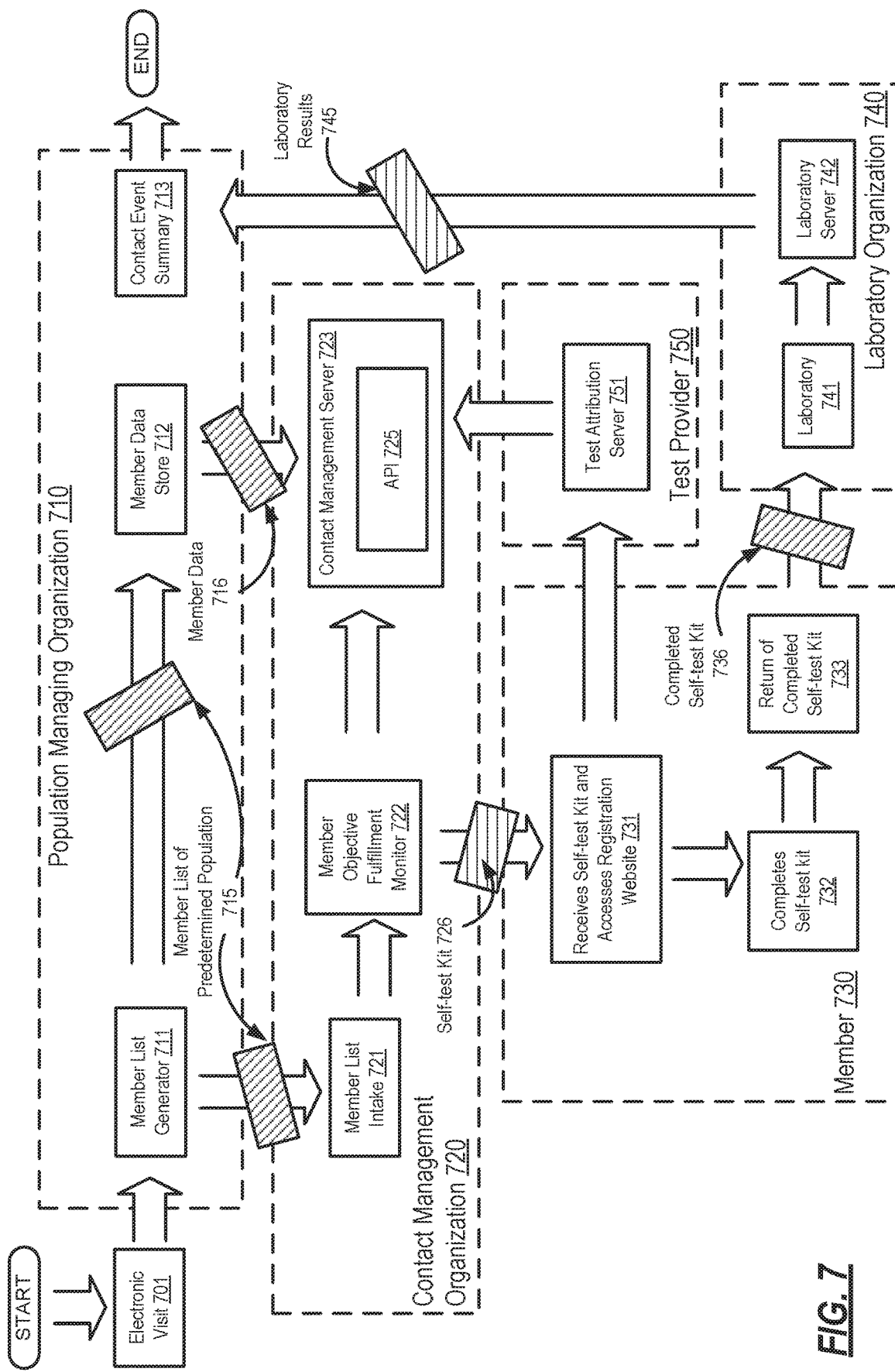
FIG. 7 shows an example in accordance with one or more embodiments.

Turning to FIG. 7, FIG. 7 provides an example of a contact management workflow in accordance with one or more embodiments. The following example is for explanatory purposes only and not intended to limit the scope of the disclosed technology. In FIG. 7, after an electronic visit (701), a population managing organization (710) uses a member list generator (711) to generate a member list (715) of a predetermined population. The member list (715) may be transmitted to a member list intake (721) for a contact management organization (720), e.g., that provides an API for member lists. Likewise, the member list (715) may also be transmitted to a member data store (712). At the member data store (712), the member list (715) may be used with a pop network protocol to transmit member data (716) to a contact management server (723) hosted by a contact management organization (720) and through an application programming interface (API) (725). For example, the member list (715) and the member data (716) may be used by the contact management server (723) to perform contact events regarding a particular population include member (730).

Keeping with the contact management organization (720) in FIG. 7, the member list intake (721) may transmit the member list (715) to a member objective fulfillment monitor (722) that is responsible for delivering self-test kits (e.g., self-test kit (726)) to population members (e.g., member (730)). According the member objective fulfillment monitor (722) may notify the contact management server (723) when a self-test kit is initially sent to member (730) as well as providing tracking information to the contact management server (723) regarding the package. In Block 731 of FIG. 7, the member (730) receives the self-test kit and proceeds to access a registration website, i.e., test attribution server (751) operated by the test provider (750). The test attribution server (751) may then notify the contact management server (723) of the registration of member (730) through the API (725). Returning to member (730), the member (730) may complete the self-test kit in Block 732 and return the completed self-test kit in Block 733. Thus, the completed self-test kit (736) may be shipped to laboratory (741) that is operated by the laboratory organization (740). Once the laboratory server (742) obtains the laboratory results (745) from the laboratory (741), the laboratory results (745) may be transmitted to the population managing organization (710) to form a portion of a contact event summary (713). In some embodiments, the laboratory results (745) may be transmitted to the contact management server (723), but will not in many cases based on privacy compliance regulations.

In some embodiments, contact types include Secure email, facsimile (fax) transmissions, and other document transmissions. For example, a contact event may include transmitting third party content using one or more contact types described through this disclosure. Likewise, some embodiments include integration with third party content APIs, such as to provide contact event status updates and test kit registration data. Some embodiments have automated data integration between contact management servers and laboratories and electronic health record (EHR) systems. Likewise, some embodiments include user controls that provide users with the functionality to specifically administer patient contact management workflows over time.

In some embodiments, a contact event corresponds to a secure end-to-end messaging of members in a particular population. For example, a contact management server may trigger contact events based on secure communication protocols. Thus, member security may be implemented, while also optimizing a member's experience and removing impediments to engagement with various entities in the contact management workflow. In particular, members may not want to login into a secure site, such as an EHS portal provided by an EHS portal server, in order to view content or read messages. In other words, members may want to limit their communication to their existing methods of communication. Accordingly, a contact event may be secure and compliant with various privacy laws. Thus, some embodiments are contemplated that allow for portal-style access to view secure emails in addition to transport layer security (TLS) delivery options. In some embodiments, a member or a population managing organization may be able to determine whether individual contact events will include TLS-only events, TLS events and/or portal events, or portal-only events. Accordingly, users may be able to use a custom authentication challenge when using the portal, such as knowledge factors that include (Enter medical record number (MRN), date of birth (DOB), etc.)

In some embodiments, contact events include prescriber facsimile (fax) bursts to one or more facsimile machines. For example, a contact management server may perform an automated workflow that implements a fax burst event in response to a user request. A fax burst may include consistent and on-going fax messages. Thus, a fax contact event may be an available option within a user interface or a core system.

In some embodiments, contact events are integrated directly with EHR servers and laboratory servers. For example, various EHR systems and lab providers in order to send and receive data directly when appropriate. For example, rather than transferring data via a flat file that involves import/exports by different entities, a contact management server may be able obtain and transmit data while being blind to updates in an EHR system. Some embodiments may use a third-party provider for EHR/lab connectivity, where API interfaces are used with a the third-party provider. In some embodiments, push points are used to transmit data into the EHR systems and/or laboratory systems. Furthermore, some embodiments include using pull points for transmitting data from EHR systems and/or laboratory systems. Thus, direct data queries may be performed with respect to EHR systems or laboratory systems.

In some embodiments, branching workflow paths and member list adjustments are performed during a contact management workflow. For example, member lists may be adjusted based along with contact sequences for individual members and/or populations. In particular, members may have changes that make them no longer relevant to a particular workflow, e.g., a patient receiving medical treatment joins a different healthcare provider from the population management organization using the contact management workflow. Likewise, a workflow may require more nuances than batch processing may provide, and thus some embodiments may handle each member as an individual element within the workflow. Without doing so, members may continue to receive irrelevant communications or could miss out on a direct connection with a population managing organization.

Some embodiments include a single-entity processing through workflow, where each member is a single entity that allows them to move to experience a contact sequence of events tailored for them individually. A single-entity workflow may branch into separate paths based on applying logic to contact result data, for example. Thus, a member may have the ability to branch the single-entity workflow into separate paths based on activities that occur along the way, such as laboratory results.

In some embodiments, end users may search for content and generate special contact events using third party content dynamically, as well as other dynamic content creation tools. Accordingly, a population managing organization may transmit a request to a contact management server to adjust message content and/or format. Thus, third party content API Integration may provide the functionality to search for desired content desired as well as insert desired contact in contact event messages. In some embodiments, a contact management server may provide the ability to generate and/or adjust content in a graphical user interface editor (such as a central dashboard) using one or more generic templates.

Likewise, some embodiments include the ability to modify member data, such as manually through a user interface or through one or more automation processes, such as by connecting a member data store to an API.

Some embodiments include virtual physician oversight. For example, some health systems may have their own captive process for cycling needed at-home test fulfillment through a physician's review process so that any resulting order (e.g., provided to a contact management server) that is receive has associated with it a physician's order, a standing lab order and the associated coding required in front line systems like the electronic health record. In some embodiments, one or more servers may support orders by prospective clients (e.g., accountable care organizations, insurance payers, employer groups) that may not have the capability to support such a system. Thus, some embodiments automate a workflow (e.g., using an API) such that a population managing organization's system may transmit a list of candidate recipients for test fulfillment. The list of candidate recipients may be passed to a virtual telehealth provider who then reviews and approves/declines the order, thereby providing (upon approval) the back-end transaction specifics for proceeding with a fulfillment (e.g., a pharmacy, lab order, physician provider ID, etc.).

Moreover, embodiments using virtual physician oversight may include one or more of the following: (1) non-integrated health Plans may require process to review target population list and issue lab orders for lab tests; (2) once candidate target population list is uploaded, it may be passed to virtual health provider; (3) connect to API for data exchange, both inbound and outbound HL7 (or other data formats); (4) physician review may occur and issuance of lab request orders (e.g., data transactions and associated PDFs of physician orders); (5) process may pass the target list to a virtual health provider for lab orders; return scripts and documents come back to a navigation tool; (6) any patients for whom screening was declined may be routed back to a plan for action; (7) a contact management server may store an archive of lab requests and results; (8) plans accessing may only have access to that plan's member data; (9) archival documents may be selected for export to remote EHR using API tool for this process; and (10) data may be online for 3 years+current YTD, archived for 10 years, or longer as required by user systems.

Some embodiments include live call integration. In addition to text-to-voice IVR call automation capability, for example, some embodiments may provide the capability to route a task list or workflow queue for live agent contact with members (e.g., patients) on behalf of a population managing organization's systems. The providers of the actual calls may be any combination of professional call centers, virtualized clinical support staff resources, or a UI enabling the population managing organization's system themselves to access servers to drive call center queues and record outcomes, log and/or close events.

Furthermore, some embodiments provide data integration between various entities. For example, a virtual health/telehealth entity (e.g., through an API) may have an API that handles outbound candidate target population lists for FIT and inbound physician lab order (or not)—transactions and PDF artifacts and lab test results/dates. In another embodiment, an email entity's API may have outbound email lists (with template IDs, by client, by outreach) and inbound send/receive/open/bounce results, dates, and/or times. In another embodiment, IVR/robocalls entity have provide an API that handles outbound call lists (e.g., with script IDs, by client, by outreach) and inbound call log results, dates, and/or times. In another embodiment, an EHR connectivity entity may have an API that integrates outbound PDF and other document artifacts documenting patient outreach touches per entity rules. In another embodiment, SMS text entity may have an API that integrates outbound text msg lists (e.g., with template IDs, by client, by outreach) and inbound send/receive/open/bounce results, dates, and/or times. Finally, in another embodiment, a live call entity may use secure File transfer protocol (sFTP) ETL batch files for integrating outbound call lists (e.g., with script IDs, by client, by outreach), enabling clinical staff to initiate calls to members, and/or inbound call log results, dates, and/or times. ETL is a type of data integration that refers to the three steps (i.e., "ETL" refers to "extract, transform, load") used to blend data from multiple sources.

In some embodiments, live call integration may use sFTP transmission of a batch of live calls queued for action to provider vendor, identifying client Plan, member call information and script to be executed. In another embodiment, live call integration may use a vendor-facing web page through which backlog lists of patients/members queued up for live follow-up calls would be presented for action.

Some embodiments may include EHR integration. For example, EHR integration may include one or more of the following: (1) connector APIs can enable access that can homogenize the connection to almost all industry EHRs; (2) if used, applicable fulfillment archival PDFs will be transmitted to target provide EHR/patient chart for frontline access; (3) a contact management server may store an archive of what got transmitted to EHR; (4) plans accessing must only have access to that Plan's member data; (5) archival documents may be selected for export to remote EHR using API tool for this process; (6) data may be online for 3 years+current YTD, archived for 10 years; and (7) two way transmissions may be possible.

While the disclosure has been described with respect to a limited number of embodiments, those skilled in the art, having benefit of this disclosure, will appreciate that other embodiments can be devised which do not depart from the scope of the disclosure as disclosed herein. Accordingly, the scope of the disclosure should be limited only by the attached claims.

What is claimed is:

1. A method, comprising:
    obtaining, by a contact management server, member data of a predetermined population, wherein the member data describes at least one member that performed an electronic visit to a virtual telehealth provider;
    obtaining, by the contact management server and using an application programmable interface (API), a notification from a test attribution server that the at least one member is registered for a self-test kit;
    determining, by the contact management server, a contact sequence for contacting a user device, wherein the contact sequence corresponds to a plurality of different contact types that are used according to a predetermined priority ranking, and wherein the user device is associated with the at least one member of the predetermined population;
    determining, by the contact management server, whether the self-test kit for the at least one member is delivered to a testing facility;
    determining, by the contact management server and automatically in response to determining that the self-test kit has not been delivered to the testing facility and based on the predetermined priority ranking and the member data, a selection of a first contact type for contacting the user device; and
    transmitting, by the contact management server, a first command that triggers a first contact event of the user device based on the selection of the first contact type.

2. The method of claim 1,
    wherein the predetermined priority ranking determines an order that the plurality of different contact types are used for a plurality of contact events, and wherein the plurality of different contact types comprises a short message service (SMS) text message, a non-human telephone call, and an email notification.

3. The method of claim 1, further comprising:
determining whether the first contact event resulted in satisfying a predetermined member objective; and
transmitting, in response to determining that the first contact event fails to result in the predetermined member objective, a second command that triggers a second contact event of the user device based on the first contact type of the first contact event.

4. The method of claim 1, further comprising:
determining that a predetermined member objective is satisfied regarding the at least one member in response to at least one of a plurality of scheduled contact events, wherein the contact sequence comprises a plurality of scheduled contact events regarding the user device; and
terminating, in response to the predetermined member objective being satisfied, remaining contact events for the user device within the contact sequence.

5. The method of claim 1, further comprising:
determining a predetermined time to perform the first contact event of the user device,
wherein the first command to trigger the first contact event of the user device is transmitted automatically at the predetermined time.

6. The method of claim 1, further comprising:
obtaining a request to adjust the contact sequence to produce an adjusted contact sequence,
wherein at least one contact type in the contact sequence is excluded from the adjusted contact sequence.

7. The method of claim 1, further comprising:
obtaining a notification from a server that no self-test kit has been delivered to a testing facility; and
transmitting, automatically based on the predetermined priority ranking, a second command that triggers a second contact event of the user device,
wherein the second contact event being a second contact type that is different from the first contact type.

8. The method of claim 1, further comprising:
obtaining, from an electronic health record (EHR) portal server, contact information regarding the user device, and
wherein the first contact event is performed using the contact information.

9. The method of claim 1,
wherein the plurality of different contact types comprises:
a secure email message that is transmitted through a transport layer security (TLS) protocol;
a message that is transmitted to an electronic health record (EHR) portal; and
a plurality of messages that are transmitted to an email account using the TLS protocol and the EHR portal.

10. The method of claim 1,
wherein the first contact type is a facsimile message, and
wherein the first contact event comprises a burst of facsimile messages to a predetermined facsimile machine.

11. A method, comprising:
obtaining, by a contact management server, member data of a predetermined population and member data, wherein the member data describes at least one member that performed an electronic visit to a virtual telehealth provider;
obtaining, by the contact management server and using an application programmable interface (API), a notification from a test attribution server that the at least one member is registered for a self-test kit;
obtaining, by the contact management server, contact event result data regarding a plurality of user devices, wherein the contact event result data describes results of a plurality of previous contact events regarding a plurality of self-test kits;
determining, by the contact management server and based on the contact event result data, whether the self-test kit for the at least one member is delivered to a testing facility;
determining, by the contact management server, a contact sequence for contacting the plurality of user devices, wherein the contact sequence corresponds to a plurality of different contact types that are used according to a predetermined priority ranking;
determining, by the contact management server and automatically in response to determining that the self-test kit has not been delivered to the testing facility based on the contact event result data, the member data, and the contact sequence, a first contact type that is different from a second contact type associated with at least one previous contact event; and
transmitting, by the contact management server, one or more commands that trigger one or more contact events based on the first contact type.

12. The method of claim 11,
wherein the predetermined priority ranking determines an order that the plurality of different contact types are used for a plurality of contact events, and
wherein the plurality of different contact types comprises a short message service (SMS) text message, a non-human telephone call, and an email notification.

13. The method of claim 11,
wherein the plurality of different contact types comprises:
a secure email message that is transmitted through a transport layer security (TLS) protocol;
a message that is transmitted to an electronic health record (EHR) portal server; and
a plurality of messages that are transmitted to an email account using the TLS protocol and the EHR portal server.

14. The method of claim 11, further comprising:
obtaining, from an electronic health record (EHR) portal server, contact information regarding the plurality of user devices, and
wherein the one or more contact events are performed using the contact information.

15. A system, comprising:
a plurality of user devices coupled to a network, wherein each user device is associated with a respective member of a predetermined population;
a contact management server coupled to the network, and wherein the contact management server is configured to:
obtain member data of the predetermined population, wherein the member data describes at least one member that performed an electronic visit to a virtual telehealth provider;
obtain, using an application programmable interface (API), a notification from a test attribution server that the at least one member is registered for a self-test kit;
determine a contact sequence for contacting a user device among the plurality of user devices, wherein the contact sequence corresponds to a plurality of different contact types that are used according to a predetermined priority ranking, determine whether the self-test kit for the at least one member is delivered to a testing facility, determine, automatically in response to determining that the self-test kit has not been delivered to the testing facility and based on the member data, a selection of a contact type for contacting the user device using the contact sequence, and transmit a command that triggers a contact event of the user device based on the contact type.

16. The system of claim 15, wherein the contact management server is further configured to obtain a request to trigger the contact event of the user device, and wherein the request to trigger the contact event is triggered automatically at a predetermined time.

17. The system of claim 15, wherein the contact management server is further configured to determine that a predetermined member objective is satisfied regarding the respective member in response to one or more previous contact events.

18. The system of claim 15, further comprising:
an electronic health record (EHR) portal server coupled to the contact management server, wherein the EHR portal server transmits member data regarding the predetermined population to the contact management server, and wherein the contact management server transmits contact event result data and commands to trigger contact events to the EHR portal server.

\* \* \* \* \*